United States Patent
Campman (10) Patent No.: US 7,279,688 B2
(45) Date of Patent: Oct. 9, 2007

(54) ARSON AND FORENSIC SCANNER HAVING A HYDROCARBON GAS DETECTOR WITH A DETACHABLE COLLECTOR CONE AND KIT ASSEMBLY

(76) Inventor: James P. Campman, P.O. Box 167, Transfer, PA (US) 16154

( * ) Notice: Subject to any disclaimer, the term of this patent is extended or adjusted under 35 U.S.C. 154(b) by 52 days.

(21) Appl. No.: 11/271,937

(22) Filed: Nov. 14, 2005

(65) Prior Publication Data

US 2006/0218987 A1    Oct. 5, 2006

Related U.S. Application Data

(60) Provisional application No. 60/667,690, filed on Apr. 4, 2005.

(51) Int. Cl.
*G01N 21/64* (2006.01)
(52) U.S. Cl. .................................... 250/461.1; 250/301
(58) Field of Classification Search ............. 250/461.1, 250/301
See application file for complete search history.

(56) References Cited

U.S. PATENT DOCUMENTS

| | | | | |
|---|---|---|---|---|
| 3,950,739 | A | * | 4/1976 | Campman .................. 340/628 |
| 4,293,225 | A | * | 10/1981 | Wheaton et al. ............. 356/417 |
| 4,897,551 | A | * | 1/1990 | Gersh et al. .............. 250/461.1 |
| 5,581,356 | A | * | 12/1996 | Vezard ....................... 356/418 |
| 5,974,860 | A | * | 11/1999 | Kuroda et al. ................. 73/40 |
| 6,177,678 | B1 | * | 1/2001 | Brass et al. .............. 250/461.1 |
| 7,122,812 | B2 | * | 10/2006 | Kalley et al. ........... 250/504 R |
| 2004/0119975 | A1 | * | 6/2004 | Ostler et al. ................ 356/318 |
| 2005/0247892 | A1 | * | 11/2005 | Davis ..................... 250/504 H |

* cited by examiner

*Primary Examiner*—Constantine Hannaher
(74) *Attorney, Agent, or Firm*—Daniel K. Dorsey (57) ABSTRACT

A simple and reliable portable flashlight shaped instrument that combines in a first embodiment an array of a combination of ultraviolet, white and multicolor LED arrays in combination with a broad band hydrocarbon gas detector and, in a second embodiment, a combination of ultraviolet, white and infrared LED arrays. There is also a readily attachable collector cone with a plurality of magnifying lenses, which are removable and a kit assembly with an extender sleeve for the collector cone, and a collector cone heater chamber. Many types of hydrocarbons fluoresce under the influence of an ultraviolet light. This rugged constructed instrument will find trace amounts of suspect materials and is extremely easy to use. The built in gas detector is cable of detecting trace amounts of accelerants days after a fire.

18 Claims, 10 Drawing Sheets

ARSON AND FORENSIC SCANNER HAVING A HYDROCARBON GAS DETECTOR WITH A DETACHABLE COLLECTOR CONE AND KIT ASSEMBLY

CROSS-REFERENCE TO RELATED APPLICATIONS

This application claims the benefit of U.S. Provisional Application No. 60/667,690, filed Apr. 4, 2005.

BACKGROUND OF THE INVENTION

1. Field of the Invention

The present invention relates to arson and forensic scanners as well as hydrocarbon gas detectors with detachable collector cones. More specifically, the present invention relates to a portable detection instrument being a flashlight type apparatus with an array of LEDs including multicolored, white and ultraviolet LEDs with a hydrocarbon gas detector and a readily detachable collector cone with three different removable magnifier lenses as well as a kit assembly for arson and forensic investigations.

2. The Prior Art

U.S. Pat. No. 3,903,726 to Hirosawa et al. is directed to a gas detecting device for detecting alcohol fumes. The device of Hirosawa et al. has a tubular body with a gas inlet aperture and a battery-actuated suction fan for aspirating the gas over a gas-sensitive semiconductor element. The device also has an indicator lamp for emitting a signal in response to the semiconductor element sensing the presence of alcoholic fumes. The device is used primarily by a police officer to examine an operator of an automobile to determine the operator's level of intoxication.

In U.S. Pat. No. 4,617,821 to Yokoyama et al. flashlight shaped gas detecting device is described. The device is utilized for detecting liquor contained in expired gas of driver of a car. There is an inlet described for sucking expired gas of an object person and an air blower for attracting the expired gas. A gas detecting element detects the liquor in the expired gas. The device further includes an illuminating section. The device provides two functions. It illuminates and detects. Accordingly, the device eliminates the need to hold a flashlight and a gas detecting device.

U.S. Pat. No. 5,839,821 to LeZotte is a flashlight that has a light source and a detector. The detector detects emissions from the surroundings. The flashlight includes a speaker for outputting a tone. The tone has a frequency that is dependent on illuminates of a series of LED elements representing intensity of electromagnetic emissions. In one of the described embodiments, the flashlight includes infrared detectors for detecting infrared thermal emissions. The flashlight is designed to supplement a conventional flashlight in order to assist police officers and emergency personal to discover the whereabouts of a suspect at night in thick vegetation.

United States Patent Application No. US 2002/0093649 to Brass illustrates and describes a flashlight shaped apparatus with at least one LED emitting near ultraviolet or ultraviolet radiation to excite a luminescent material for non-destructive fault detection. In other words, the apparatus uses light sources and dyes to locate faults in machinery. The dye is poured into a system such as an air conditioning unit and the LED emits ultraviolet radiation in a range of 385 to 465 nanometers to luminate areas where faults such as leaks or stress fractures may be in the air conditioning unit.

United States Patent Application No. US 2002/0223342 to Kilpstein et al. shows and describes a flashlight device with a plurality of lamps that have light emitting diodes for producing radiation suitable to excite fluorescent materials. The device is used for detecting leaks in systems such as refrigeration systems wherein the fluorescent materials is placed in the refrigeration system having fluid under pressure. The fluorescent material becomes a gas that can be seen by the device with the lamps in order to detect leaks.

None of the noted prior art flashlight type devices can detect trace amounts of forensic evidence such as fingerprints, semen, saliva, or blood days after an incident and with the gas/hydrocarbon sensor trace amounts of accelerants can be detected days after a fire. Accordingly, a need exists for a portable flashlight shaped detector that can be utilized for forensic and arson investigations.

SUMMARY OF THE INVENTION

Ultraviolet light is a simple, reliable, cost effective method of heat detection that is too frequently over-looked in arson investigation. Ultraviolet light not only assists in rapidly locating accelerants residues, it also assists in locating the point of origin of the fire. The color, which accelerants glow is affected by heat exposure. In other words, the longer an accelerant is exposed to heat (i.e., the origin), the more differentiated its fluorescence color will be from other less exposed areas. Evidence of accelerants is almost always invisible to the naked eye after they have been absorbed in a fire. However, the areas tarnished by accelerants are easily discernible under ultraviolet light.

Volatile hydrocarbons such as gasoline, kerosene and other petroleum fractions, benzene, acetone, grease, lard, vegetable oils, paints, and others fluoresce when exposed to ultraviolet light. In addition, ultraviolet light can be helpful in locating fragments incendiary devices since explosive wrappings are frequently fluorescent. The use of ultraviolet light enables the investigator to accurately identify locations where samples should be collected for further laboratory analysis. Samples collected in cans and plastic evidence bags can then be heated in warm water to from condensation. Latent accelerant residue may then be brought to the surface and seen under ultraviolet light.

Ultraviolet light is not contingent upon wind conditions. However, in order to successfully use ultraviolet light at a fire scene, ambient light must be reduced to a minimum. Usually, this is done, by covering windows and other exposed areas, with an opaque sheeting such as black plastic. Thus, it is important to put collected samples in a properly sealed air-tight container, and properly label the evidence before dispatching and storing via the recommended procedures so as to not contaminate the collected material.

Ultraviolet light is a band of wavelengths (electromagnetic radiation) between visible light and x-rays. Ultraviolet light is typically divided into three ranges, long-wave, which is 315 nm and above, mid-range, which is 280 nm-315 nm, and short-wave, which is 280 nm and below. The chief source of natural ultraviolet light is the sun. In fact, 9% of all energy emitted by the sun is ultraviolet, most of which is in the region of 300 nm to 400 nm. Fluorescence in materials is caused by some impurity, frequently referred to as "activators" or "activating agents." All matter is made of atoms. All atoms are made of electrons which obit around a nucleus. In the case of many accelerants, if these electrons are exposed to ultraviolet light, they absorb energy, move violently, and jump outward form their normal orbit. As the electrons leave their orbit, another electron is pulled down form its orbit to maintain the electrical balance. This movement produces energy and it is this energy, which is seen as fluorescence. Fluorescence occurs only while the material is being activated by ultraviolet light. Phosphorescence occurs when a material retains and releases, in the form of visible light, some of the energy it receives during the period of activation called fluorescence, after the activating ultraviolet light source has been removed. This released radiation following the period of activation may persist for periods from a quarter of a second to a matter of many hours. The light given off during phosphorescence is quite dim compared to fluorescence. Thus, ultraviolet light can be or great assistance in bomb investigation. Many ingredients of explosives fluoresce, such as nitrates, sulfur, fuel oil, and paraffins. Metal fragments with traces of these residues can frequently be found with the use of ultraviolet light as well as Molotov cocktail type containers.

Accordingly, a need exists for a simple and reliable portable flashlight shaped instrument that combines an array of at least eight ultraviolet LEDS and at least twenty-four colored LEDs in combination with a hydrocarbon gas detector. The portable detection instrument of the present invention combines an array of eight ultraviolet and eight white LEDs in combination with four red LEDs, four blue LEDs, four yellow LEDs and four green LEDs as well as a hydrocarbon detector. It is well known that many types of hydrocarbons fluoresce under the influence of ultraviolet and multicolor light. This rugged constructed instrument of the present invention detects trace amount of suspect materials and is extremely easy to use. The built in hydrocarbon gas detector is capable of detecting trace amounts of accelerants days after a fire, and because the detector of the present invention can be used with an environmental chamber assembly during field use, arson/forensic evidence can more readily be detected.

Accordingly, it is an object of the invention to provide an apparatus for arson and forensic inspection, the apparatus includes an extremely rugged enclosure, a multitude of optical radiators, the multitude of optical radiators ranging from ultraviolet to infrared, a microprocessor positioned in the rugged enclosure for controlling the apparatus for arson and forensic inspection and infrared communication.

It is another object of the invention to provide an apparatus having a rugged, flashlight like enclosure for containing a hydrocarbon gas or vapor detector in combination with a plurality of optical light radiators that range from ultraviolet (UV), visible light (VL) and infrared (IR) light, wherein the robust, rugged, flashlight like enclosure contains an array of solid state light sources, the solid state light sources radiate light that ranges from the ultraviolet through visible and into the infrared spectrum, the flashlight like enclosure contains a hydrocarbon gas sensor for responding to greater than 100 hydrocarbon based gases, and contains a power on/off switch in combination with a sensitivity control and microprocessor electronics, the push button switch controls by turning on and off various arrays of the solid state light sources having light emitters in combination with the hydrocarbon gas sensor, and the push button switch permitting a mixing of different wavelengths of light and colors emitted from the solid state arrays under a microprocessor control.

A further object of the invention is to provide an apparatus whereby encoding the invisible (to the human eye) light, for emitting arrays for secured optical communications.

A still further object of the invention is to provide an apparatus whereby housing the hydrocarbon gas sensor in a center of a scanning head of the flashlight type enclosure, a captivating hood is realized for capturing of gas or volatiles.

Another object of the invention is to provide a hydrocarbon gas detector and optical scanner under the control of a dedicated on-board computer, the on-board computer having a microprocessor to provide functionality and detection of suspect material, and the microprocessor being preprogrammed for receiving code encryption of UV, infrared, and white light, and for mixing UV, infrared and visible light in a manner that encodes all signals via optical encryption.

A still further object of the invention is to provide an apparatus comprising an optical signaling device that has a time of day location and other type information encoded within a signaling array, the optical signaling device housing a hydrocarbon gas sensor in a center of a scanning head of a flashlight type enclosure and forming a captivating hood for easy capturing of hydrocarbon gas or vapors. The apparatus comprising means for visually indicate a mode of operation, wherein the signaling device provides visual and audible indication when exposed to a hydrocarbon gas, wherein the signaling device includes an electronic purge for providing quick recover of the gas sensor when exposed to high concentrations of gas, and includes means for displaying results via an audible signal tones for changes of the tones and pulse rate when exposed to a gas atmosphere. The apparatus provides audible tone frequency, which increases if exposed to a gas atmosphere, wherein the apparatus further includes a voice audible recorder, wherein the apparatus includes a data logger, and wherein the apparatus being powered by disposable batteries, rechargeable batteries or line power.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Preferred structural embodiments and preferred subcomponents of this invention are disclosed in the accompanying drawings in which.

DESCRIPTION OF THE INVENTION

Further scope of applicability of the present invention will become apparent from the detailed description given hereinafter. However, it should be understood that the detailed description and specific example, while indicating a preferred embodiment of the invention, are given by way of illustration only, since various changes and modifications within the spirit and scope of the invention will become apparent to those skilled in the art from this detailed description.

Figure 1:
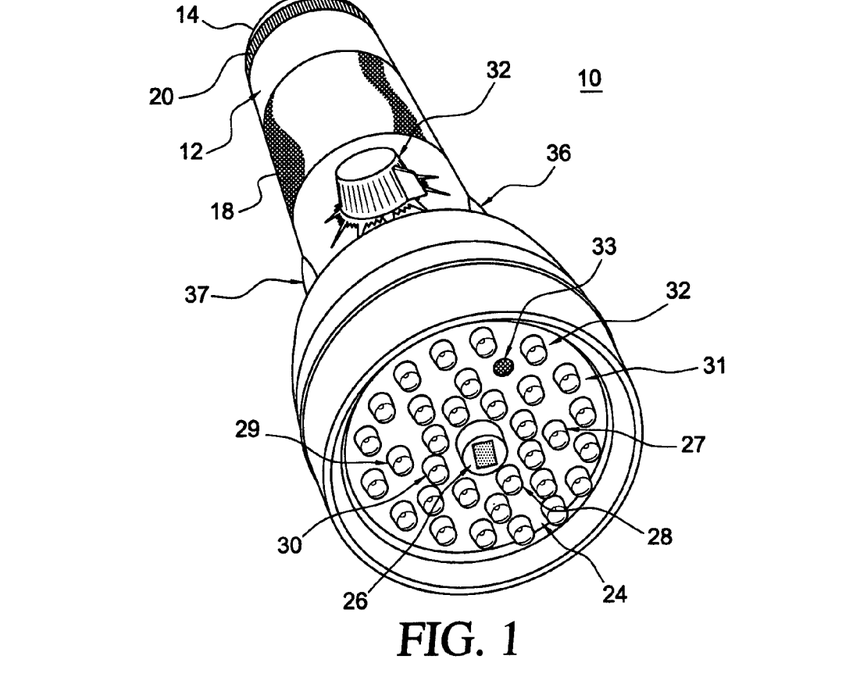
FIG. 1 illustrates a front perspective view of an arson and forensic scanner and hydrocarbon detector apparatus in accordance with a first embodiment of the present invention.
Figure 2:
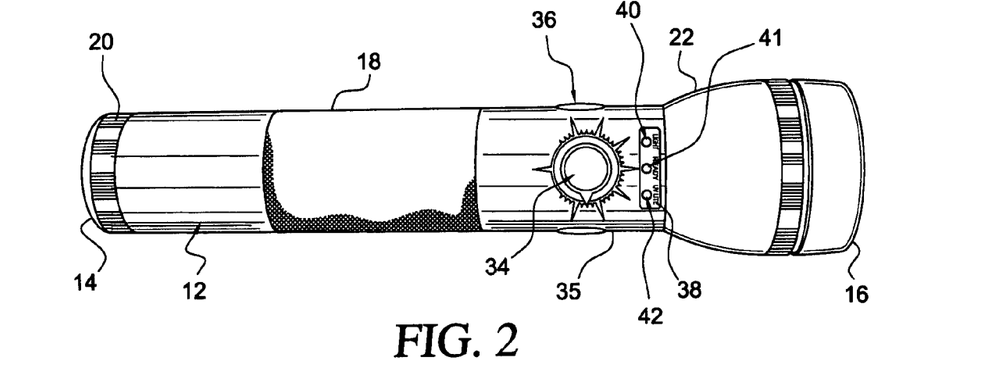
FIG. 2 illustrates a top view of the arson and forensic scanner and hydrocarbon detector apparatus in accordance with the first embodiment of the present invention.

FIG. 1 illustrates a front perspective view of the first embodiment of the arson and forensic scanner and hydrocarbon gas detector apparatus 10. FIG. 2 illustrates a top view of the apparatus 10. The first embodiment of the present invention will initially be described with reference to these two figures. The apparatus 10 is useful with forensic requirements, arson inspection requirements or both. The apparatus 10 is enclosed in an extremely rugged housing 12, which is aluminum in this first embodiment. It could also be made of steel or any other rugged material. The housing 12 is one and half inches in diameter at a rear section 14. A front section 16 of the stainless steel housing 12 is two and a quarter inches in diameter. The front section 16 forms a captive hood for capturing gas or volatiles. The entire housing 12 of the apparatus 10 is ten and three eighths inches over all, which includes a middle section 18.

The rear section 14 includes a screw off cap 20 wherein a power supply such as two long life D size batteries (not shown) can be inserted. Of course, the power supply can be disposable batteries, rechargeable batteries or line power. The front section 16 comprises a flashlight head 22 having a circular illumination section generally indicated by numeral 24. In the center of the illumination section 24, a hydrocarbon sensor 26 is mounted.

Spaced around the hydrocarbon sensor 26 are four inter arrays made up of sixteen LEDs. There are four blue LEDs 27, four amber LEDs 28, four red LEDs 29, and four green LEDs 30. Around the sixteen colored LEDs 27, 28, 29, 30 are two outer rings 31, 32. The first outer ring 31 contains eight ultraviolet LEDs and the second outer ring 32 is made up of eight white LEDs. The apparatus 10 includes a total array of eight ultraviolet LEDs and twenty-four white and multicolored LEDs. There is also a sound port 33 positioned amongst the array of thirty-two LEDs. The circular illumination section 24 is removable from the front section 16. The thirty-two multi-colored and ultraviolet LEDs are the merging of forensic wavelengths. It is well established in forensics that shorter wavelengths such as 450 nanometers (nm) are most useful in body fluid, teeth and bone fragment, bite mark and bruise work. While longer wavelengths, such as 480 nanometers (nm), are most useful in trace evidence and fingerprint work. The thirty-two multi-colored and ultraviolet LEDs supplies a unique profile of forensic wavelengths which each color to permit evidence collection.

The middle section 18 has a hydrocarbon sensitivity control switch 34. The sensitivity switch 34 is dial controlled with easily viewable graduations generally indicated by the numeral 35. The sensitivity switch 34 is adjustable over a specific range, and is used to turn the arson and forensic scanner and hydrocarbon detector 10 "on" and "off". The sensitivity switch 34 is electrically connected to the hydrocarbon sensor 26.

On either side of the sensitivity control switch 34 are buttons 36 and 37. Button 36 is a light push button. The other push button 37 is an electronic purge. The light push button 36 operates the thirty-two LEDs in the inter rings 27, 28, 29, 30 and outer rings 31, 32. Immediately above the graduations 35 of the hydrocarbon sensitivity switch 34 is a viewable tip bar indicator 38. The indicator 38 contains three indicator LEDs 40, 41, and 42. The indicator LED 40 indicates, with a white light to the user, that the thirty-two LEDs 27, 28, 29, 30, 31, 32 are active. The indicator LED 41 indicates, with a green light to the user, that the hydrocarbon sensor 26 is ready. The indicator LED 42 indicates, with a red light to the user, that the battery power is low.

In operation of the arson and forensic scanner and gas/hydrocarbon detector apparatus 10, a user rotates the hydrocarbon sensitivity control switch 34 clockwise until the white light 40 glows in the top bar indicator 38. At this point, the user pushes light button 36 and the eight white LEDs 32 are activated. The user does a second push of the light button 36 to turn "on" the eight ultraviolet LEDs 31. A third push of light button 36 activates the four blue LEDs 27. With a fourth push of the light button 36, the four red LEDs 29 are activated. The fifth push of light button 36 activates the four green LEDs 30. With a sixth push of light button 36, the four amber LEDs 28 are activated. A seventh or final push of light button 36 turns the apparatus 10 "off."

Figure 3:
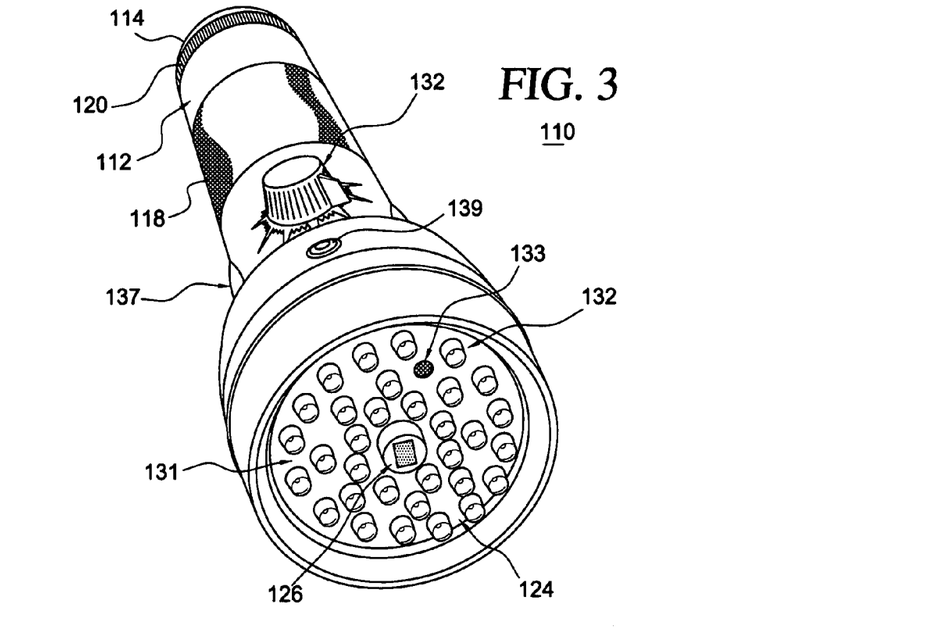
FIG. 3 illustrates a front perspective view of an arson and forensic scanner and hydrocarbon detector apparatus in accordance with a second embodiment of the present invention.
Figure 4:
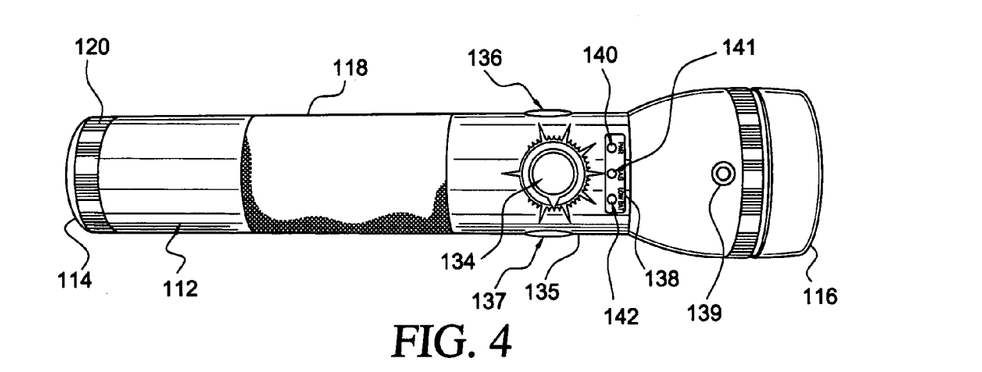
FIG. 4 illustrates a top view of the arson and forensic scanner and hydrocarbon detector apparatus in accordance with the second embodiment of the present invention.
Figure 5:
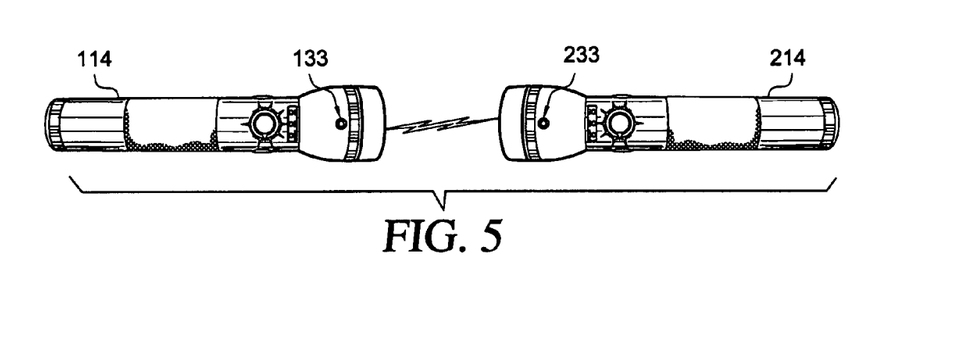
FIG. 5 illustrates a side view of two arson and forensic scanner and hydrocarbon detector apparatuses performing infrared communications in accordance with the second embodiment of the present invention.

FIG. 3 illustrates a front perspective view of the second embodiment of the arson and forensic scanner and hydrocarbon gas detector apparatus 110. FIG. 4 illustrates a top view of the apparatus 110. The second embodiment of the present invention will now be described with reference to these two figures. The apparatus 110 is useful with forensic requirements, arson inspection requirements or both. Additionally, this apparatus 110 supports infrared communications. The apparatus 110 is enclosed in an extremely rugged housing 112, which is aluminum in this embodiment. The housing 112 is one and half inches in diameter at a rear section 114. A front section 116 of the aluminum housing 112 is two and a quarter inches in diameter. The front section 116 forms a captive hood for capturing gas. The entire housing 112 of the apparatus 110 is ten and three eighths inches over all, which includes a middle section 118.

The rear section 114 includes a screw off cap 120 wherein a power supply such as two long life D size batteries (not shown) can be inserted. Of course, the power supply can be disposable batteries, rechargeable batteries or line power. The front section 116 comprises a flashlight head 122 having a circular illumination section generally indicated by numeral 124. In the center of the illumination section 124 a hydrocarbon sensor 126 is mounted. Evenly spaced around the hydrocarbon sensor 126 is an inter ring 128 made up of sixteen ultraviolet LEDs 131. Around the inter ring 128 is an outer array 130 of sixteen infrared LEDs 132 and a sound or microphone port 133.

The middle section 118 has a hydrocarbon sensitivity control switch 134. The sensitivity switch 134 is dial controlled with easily viewable graduations generally indicated by the numeral 135. The sensitivity switch 134 is adjustable over a specific range, and is used to turn the arson and forensic scanner and hydrocarbon detector 110 "on" and "off". The sensitivity switch 134 is electrically connected to the hydrocarbon sensor 126.

On either side of the sensitivity control switch 134 are buttons 136 and 137. Button 136 is a light push button. The other push button 137 is for electronic purge. The light push button 136 operates the thirty-two LEDs in the inter ring 131 and outer array 132. Immediately above the graduations 135 of the hydrocarbon sensitivity switch 134 is a viewable tip bar indicator 138. The indicator 138 contains three indicator LEDs 140, 141, and 142. The indicator LED 140 indicates, with a white light to the user, that the thirty-two LEDs of the inter ring 131 and the outer array 132 are active. The indicator LED 141 indicates, with a green light to the user, that the hydrocarbon sensor 126 is ready. The indicator LED 142 indicates, with a red light to the user, that the battery power is low.

In operation of the arson and forensic scanner and hydrocarbon gas detector apparatus 110, a user rotates the hydrocarbon sensitivity control switch 134 clockwise until the white light 140 glows in the top bar indicator 138. At this point, the user pushes light button 136 and the inter ring of sixteen ultraviolet LEDs 132 are activated. The user does a second push of the light button 136 to turn on the other ring of sixteen infrared LEDs 131. A third push of light button 136 turns the apparatus 110 "off".

Figure 6:
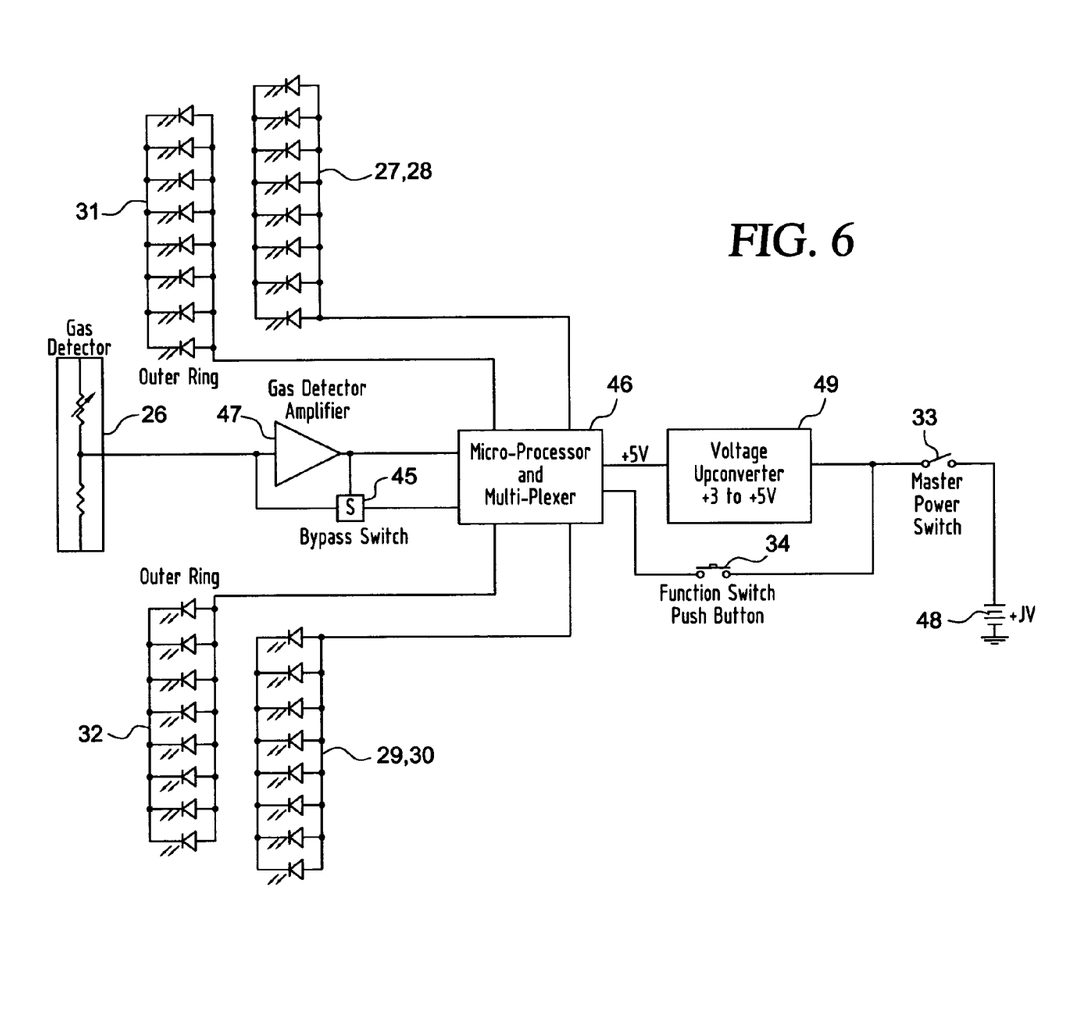
FIG. 6 illustrates a circuit diagram utilized in the arson and forensic scanner and hydrocarbon detector apparatus in accordance with the first embodiment of the present invention.

FIG. 6 illustrates a block circuit diagram of the first embodiment utilized in the arson and forensic scanner and hydrocarbon gas detector apparatus 10. The apparatus 10 can use a multitude of optical radiators ranging from ultraviolet to infrared generally indicated by numerals 26, 27, 28, 29. The apparatus 10 is controlled by a microprocessor 46, which can be readily preprogrammed. The apparatus 10 may be used as a gas detector to detect trace amounts of accelerants days after a fire. The apparatus 10 may be used at a selected color frequency for optical radiation. The housing 12 of the hydrocarbon gas detector 26 contains, in the center of the circular illumination section or scanning head 24 of the flashlight type enclosure, at the front section 16, a captivating hood for capturing gas or volatiles. The hydrocarbon gas detector 26 will respond to greater than 100 hydrocarbon based gases. The apparatus 10 utilizes the power on/off in combination with hydrocarbon gas sensitivity control switch 34 and the microprocessor electronics 46 to, through the light push button 36, control (turns "on" and "off") various arrays of light emitters in the inter ring 27, 28, 29, 30 and outer rings 31, 32 in combination with the hydrocarbon gas detector 26. The light push button 36 permits the mixing of different wavelengths of light and colors emitted from the solid-state arrays under control of the microprocessor 46. When the master power switch 33 is turned on the voltage up converter 49 is activated thus boosting the +3V supply voltage to the +5V required by the microprocessor and multiplexer 46 to activate the hydrocarbon gas detector 26. Once the apparatus 10 activated, the light button 36 can be cycled to change activate one or all of the LED arrays. When gas is present a voltage change occurs in the hydrocarbon gas detector 26. This change passes through the gas detection amplifier 47 and is amplified to a signal distinguishable to the microprocessor 46. This signal can bypass the gas detection amplifier 47 if the bypass switch 45 is activated. The apparatus 10 is simple to operate, and calibration is not required. The outer ring of ultraviolet LEDs 31 provides an ultraviolet source. The ultraviolet source causes some accelerants to glow and fluoresce when exposed to ultraviolet light.

Figure 7:
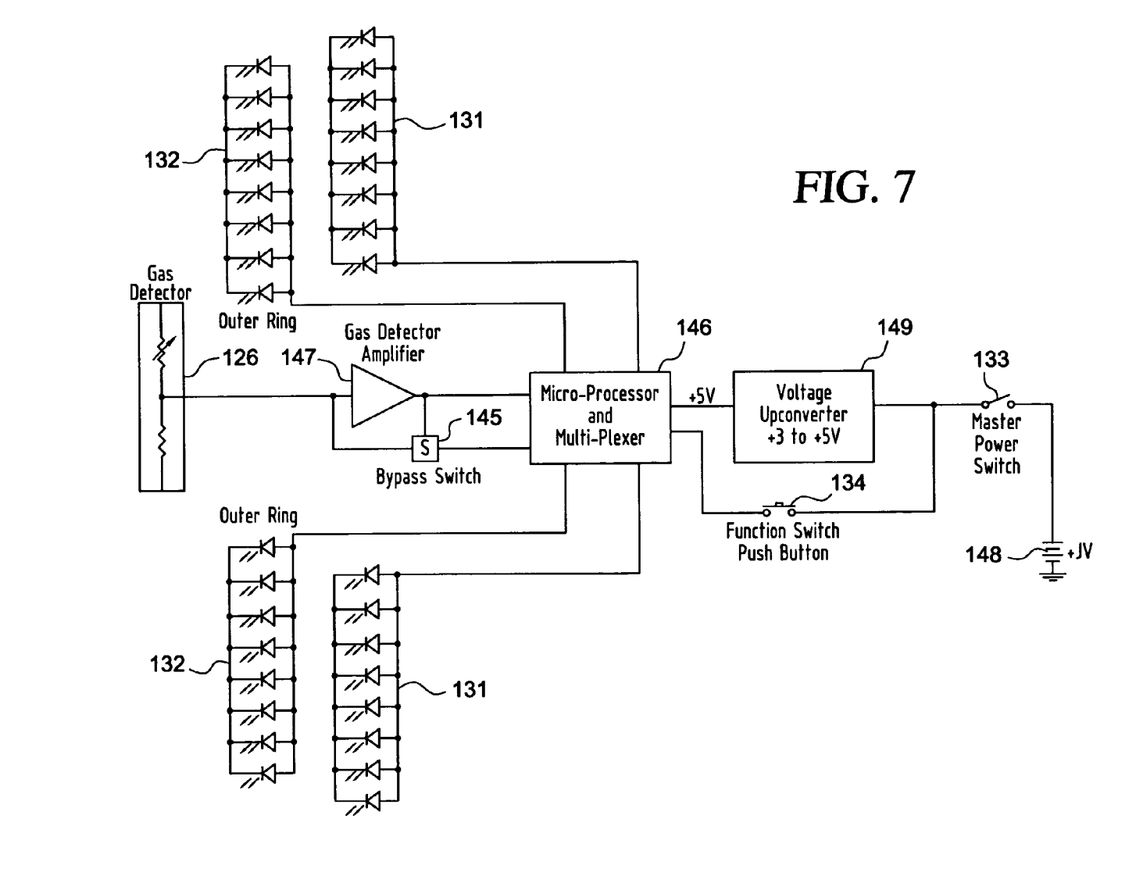
FIG. 7 illustrates a circuit diagram utilized in the arson and forensic scanner and hydrocarbon detector apparatus in accordance with the second embodiment of the present invention.

FIG. 7 illustrates a block circuit diagram utilized in the arson and forensic scanner and hydrocarbon gas detector apparatus 110. The apparatus 110 can use a multitude of optical radiators ranging from ultraviolet to infrared generally indicated by numeral 144. The apparatus 110 is controlled by a microprocessor 146, which can be readily preprogrammed. The apparatus 110 may be used as a gas detector to detect trace amounts of accelerants days after a fire. The apparatus 110 may be used at a selected color frequency for optical radiation. The apparatus 110 is easily encrypted in a serial manner that sends light bursts to a remote receiver thus ensuring secured communications. With the apparatus 110, through the programming of the microprocessor 146 and by encoding the invisible (to the human eye) light emitting arrays, covert and secured optical communications may be realized. The housing 112 of the hydrocarbon gas detector 126 contains, in the center of the circular illumination section or scanning head 124 of the flashlight type enclosure, at the front section 116, a captivating hood for capturing gas or volatiles. The hydrocarbon gas detector 126 will respond to greater than one hundred hydrocarbon based gases.

The apparatus 110 utilizes the power on/off in combination with hydrocarbon gas sensitivity control switch 134 and the microprocessor electronics 146 to, through the light push button 136, control (turns on and off) various arrays of light emitters in the inter ring 131 and outer ring 132 in combination with the hydrocarbon gas detector 126. The light push button 136 permits the mixing of different wavelengths of light and colors emitted from the solid-state arrays under control of the microprocessor 146. The sixteen infrared LEDs 132 provide a covert and secure means of voice or other communications via infrared transmitting/receiving. This is achieved by voice modulating any of the sixteen infrared LEDs through the microprocessor 146 contained within the flashlight housing 112. When the master power switch 133 is turned on the voltage up converter 149 is activated thus boosting the +3V supply voltage to the +5V required by the microprocessor and multiplexer 146 to activate the hydrocarbon gas detector 126. Once the apparatus 110 activated, the light button 136 can be cycled to change activate one or all of the LED arrays. When gas is present a voltage change occurs in the hydrocarbon gas detector 126. This change passes through the gas detection amplifier 147 and is amplified to a signal distinguishable to the microprocessor 146. This signal can bypass the gas detection amplifier 147 if the bypass switch 145 is activated. The apparatus 110 is simple to operate, and calibration is not required. The inter ring of ultraviolet LEDs 131 provide an ultraviolet source. The ultraviolet source causes some accelerants to glow and fluoresce when exposed to ultraviolet light.

The arson and forensic scanner and hydrocarbon gas detector apparatus 110 is under the control of the dedicated on board computer having the microprocessor 146 to provide functionality and detection of suspect material. The microprocessor 146 is preprogrammed for receiving code encryption of ultraviolet, infrared, and white light. The microprocessor 146 effectively mixes ultraviolet, infrared and visible light in a manner that encodes all signals via optical encryption. The optical signaling of the apparatus 110 has a time of day location and other type information encoded within the signaling array. The apparatus 110 provides visual and audible indication when exposed to a hydrocarbon gas. Additionally, with the apparatus 110 there is provided quick recover, through purge button 137, of the gas sensor 126 when exposed to high concentrations of hydrocarbon gas for use as an electronic purge.

Figure 8:
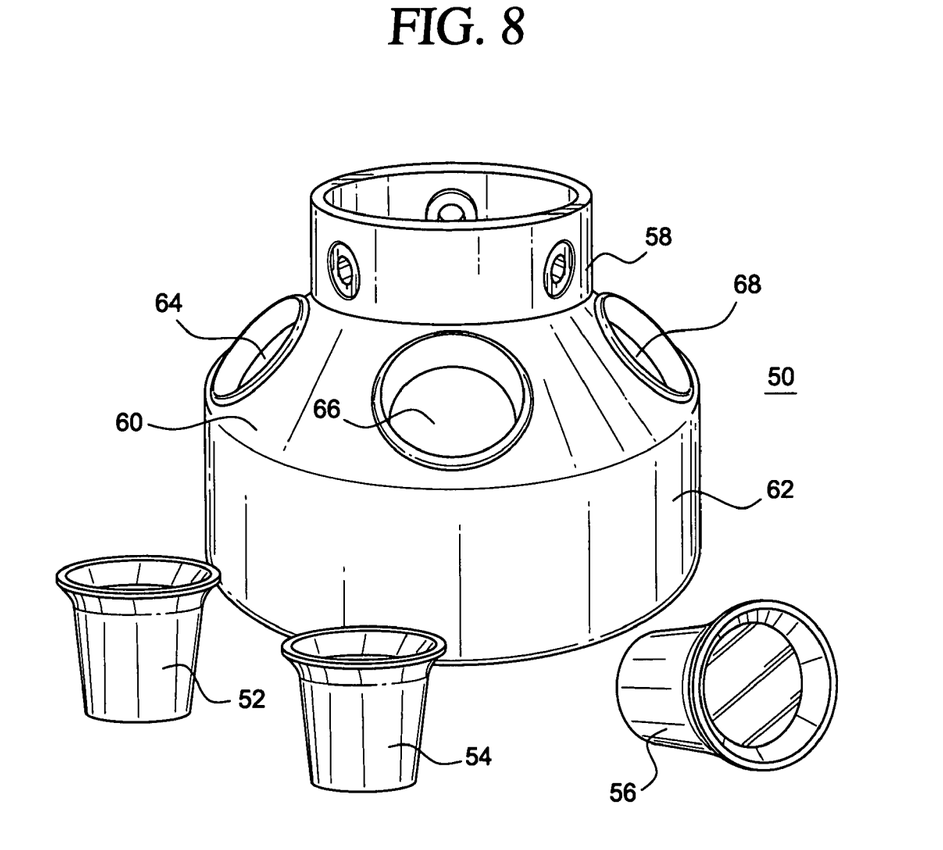
FIG. 8 illustrates a front perspective view of the collector cone and a plurality of equally spaced removable magnifying lenses in accordance with the present invention.
Figure 9:
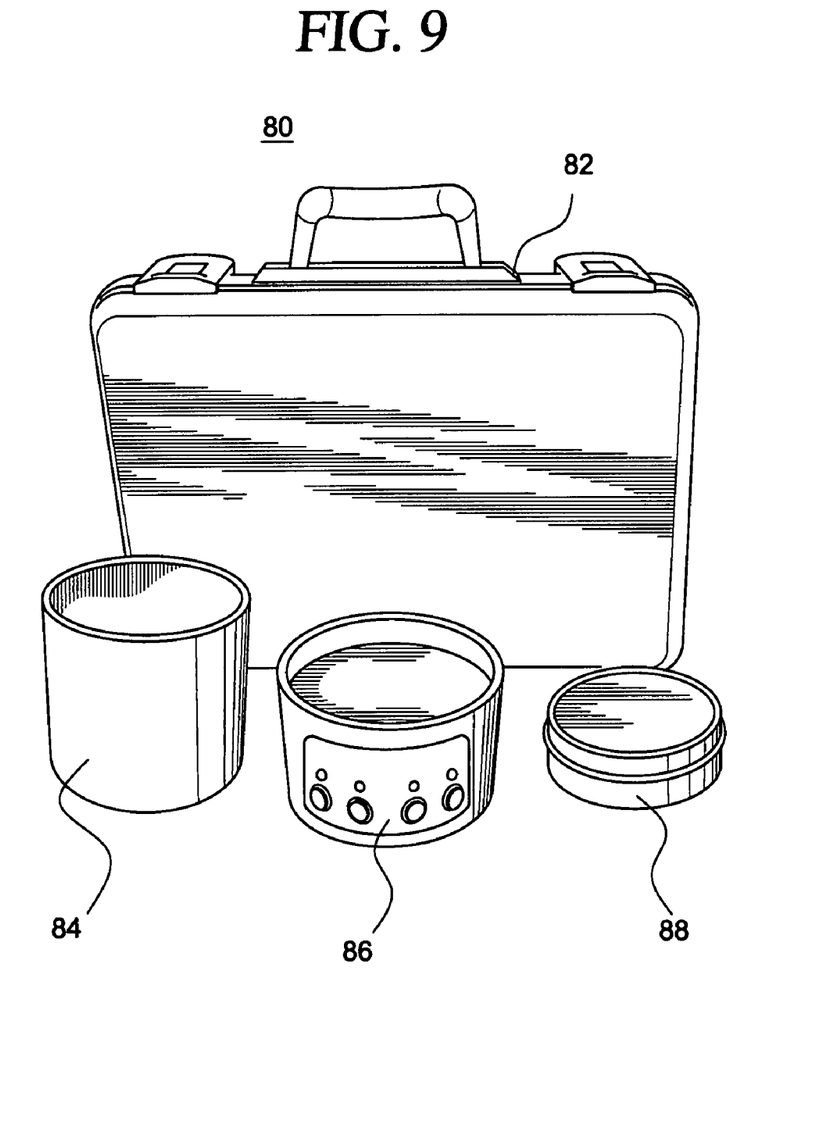
FIG. 9 illustrates a kit assembly with an extender sleeve for the collector cone, a collector cone heater chamber for hot and cold applications as well as a sample/evidence container in accordance with the present invention.

FIG. 8 illustrates a collector cone 50 made of an inert thermo plastic. Apparatus 10 can be inserted into the collector cone 50, as can apparatus 110 that will be discussed with reference to FIGS. 15, 16 and 17. The collector cone 50 provides an environmental chamber, which permits easy detection of gaseous vapors on windy days and insures a defined environment for hydrocarbon detection and visual observation of suspect material. The collector cone 50 includes readily removable magnifier lens 52, 54, and 56. Magnifier lens 52 is a power two lens, magnifier lens 54 is a power five lens, and magnifier lens 56 is a power ten lens. The cone 50 includes a circular top portion 58, which receives the front section 16 of the apparatus 10 with a secure snug friction fit with the help of rubber gripper grommets 53, 55, 57, (see FIG. 11), that fit into the three holes surrounding the top portion 58. These rubber gripper grommets 53, 55, 57 provide the friction fit for the apparatus 10. The power lenses 52, 54 and 56 are mounted on a slanted surface 60 and are equally positioned around the slanted portion 60. Slanted portion 60 connects the top portion 58 to bottom circular portion 62, which is somewhat larger than circular top portion 58.

When using the collector cone 50 with apparatus 10, forensic materials is viewed through the various magnifying lens 52, 54 and 56, the lenses help detect various suspect materials that tend to exhibit different and unique colors under the influence of the various lights provided by the apparatus 10. Burnt materials can be viewed by placing the collector cone 50 on the material and turning on the lights of the apparatus 10. The lights from LED arrays 28, 29, 30, 31, 32, 131 and 132 are visible, infrared, ultraviolet or various combinations. Many materials have visual characteristics that are altered when exposed to different temperature and lights. The apparatus 10 is portable and each weighs less than one (1) pound. In fact, with the collector cone 50 attached the apparatus 10 the weight approximately one pound and 7.6 ounces. Thus, making the apparatus 10 with the collector cone 50 extremely easy to use and carry in the field during arson or forensic investigations.

FIG. 8 illustrates a perspective view of the collector cone 50 with the magnifying lenses 52, 54 and 56 removed. The collector cone 50 can be used with or without the magnifying lenses 52, 54 and 56 when attached to the apparatus 10 or apparatus 110. When one or more of the magnifying lenses 52, 54 and 56 are removed during use, plugs (not shown) can be inserted to cover holes 64, 66 and 68, wherein hole 64 corresponds to the hole left when magnifying lens 52 is removed, hole 66 corresponds to the hole left when magnifying lens 54 is removed, and hole 68 corresponds to the hole left when magnifying lens 56 is removed. Also, there may be times, when utilizing the apparatus 10 or apparatus 110 and attached collector cone, that one or more of the holes 64, 66 and 68 are left uncovered so that some of the hydrocarbon gas escapes.

Figure 10:
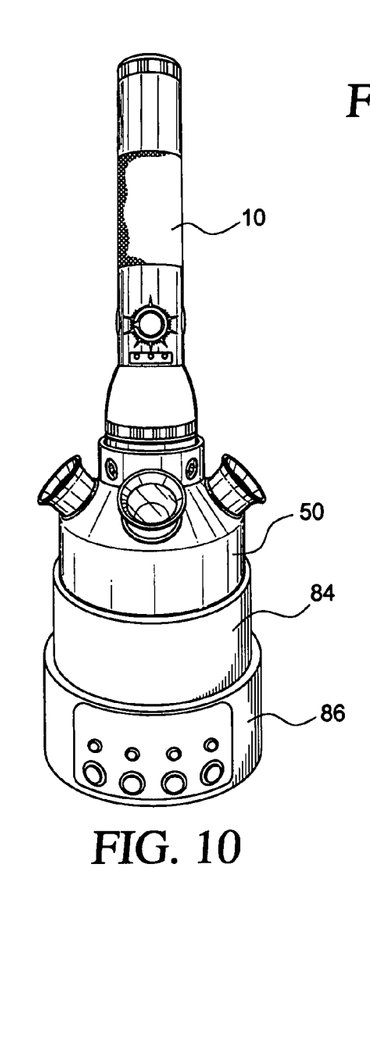
FIG. 10 illustrates a perspective view of the arson and forensic scanner and hydrocarbon detector apparatus with the extender sleeve and the collector cone heater chamber all mounted together in accordance with the first embodiment of the present invention.

FIG. 10 illustrates a kit assembly for use with the arson and forensic scanner and hydrocarbon gas detector apparatus 10 or 110. The kit assembly is indicated by reference numeral 80. The kit assembly 80 includes a carrying case 82, an extender sleeve 84 for the collector cone 50, a collector cone heater chamber 86 for hot and cold applications as well as a sample/evidence container 88. The extender sleeve 84 is made of inert thermo plastic making the extender sleeve 84 very light weight and yet extremely durable.

An example of field use during a fire investigation would be that an investigator would carry apparatus 10 and removable collector cone with the kit assembly 80 with the case 82 and its contents to detect possible accelerants after the fire. The investigator utilizing just the apparatus 10 would do a broad sweep of the burnt area. The apparatus 10 would generate an audible signal tone, through the sound port 33, that changes the tones and pulse rate when exposed to a gas atmosphere. The audible tone frequency would increase if exposed to a gas atmosphere. The sound port 32 also contains a voice audible recorder. The investigator can then attach the collector cone 50 to the apparatus 10 to begin a more focused search for detectable accelerants after the fire on a more specific burnt area. The investigator would retrieve a piece of burnt material and place the collector cone 50 with the attached apparatus 10 over the burnt material. The investigator then can use one of the magnifying lenses 52, 54 or 56 to more closely examine the accelerants.

Figure 11:
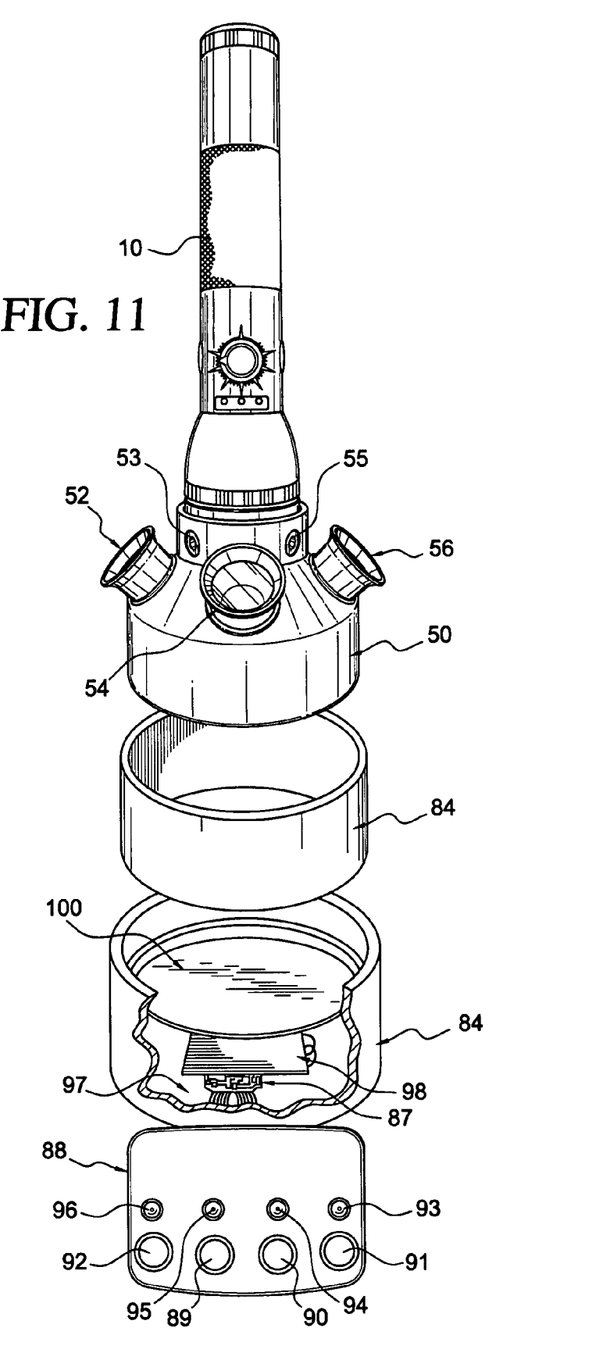
FIG. 11 a partially exploded perspective view of the arson and forensic scanner and hydrocarbon detector apparatus with the collector cone, the extender sleeve and the collector cone heater chamber and the collector cone heater chamber cut away in accordance with the first embodiment of the present invention.

With reference to FIGS. 10 and 11, FIG. 10 illustrates a perspective view of the arson and forensic scanner and hydrocarbon detector apparatus 10 with the collector cone 50, the extender sleeve 84 and the collector cone heater chamber 86 all mounted together in accordance with the first embodiment of the present invention. FIG. 11 illustrates a partially exploded perspective view of the arson and forensic scanner and hydrocarbon detector apparatus 10 with the extender sleeve 84 and the collector cone heater chamber 86 and the collector cone heater chamber 86 cut away in accordance with the first embodiment of the present invention. The collector cone heat chamber 86 can be used to provide heat or cold to suspect material or a piece of burnt material 76 that may contain entrapped hydrocarbons or other material of interest. When heat is applied to most suspected materials 76, any entrapped hydrocarbons will volatize off, thus enhancing the detection of fugitive hydrocarbons. The collector cone heater chamber 86 includes a timing circuit 87 is equipped with timers that provide five minutes, ten minutes or fifteen minutes for the application of heat or cold over a specific time period. A visible label 88 has a button 89 for the five minute timer, a button 90 for the ten minute timer, and a button 91 for the fifteen minute timer. Each of the buttons 89, 90 and 91 are electrically connected to the timing circuit 87. The label 88 also includes a reset button 92 for resetting the timing circuit 87. There are mode indicator LEDs 93, 94 and 95, above each of the timing buttons 89, 90 and 91 light for a visible indicator to the user to tell which timer is activated. The reset button 92 has its own indicator LED 96 for indicating the reset mode is activated to the user. The collector cone heater chamber 84 has a battery compartment 97 to power the timing circuit 87 and a thermo electric heater/cooler module 98. An aluminum deck 100 will heat up or cool down once the thermo electric heater/cooler module 98 is activated. The apparatus 10 is attached to the collector cone 50, which is then attached to the extender sleeve 84. The extender sleeve 84 then fits inside the collector cone heater chamber 84 after the suspect material is placed in the collector cone heater chamber 84. At this point, the investigator can either heat up or cool down the thermo electric heater/cooler module 98 and view the material through one or all of the magnifying lenses 52, 54, 56.

To locate an accelerant source, the user or investigator slowly scans area of interest. The collector cone 50 provides a controlled environment for investigating samples. If an accelerant or hydrocarbon is present, the apparatus 10 displays a flashing indicator and audible beep tones. The apparatus 10 is designed so that the more volatile the accelerant then the faster the beep rate. The apparatus 10 has excellent sensitivity and is capable of detecting hydrocarbon concentrations of less than 50 parts per million. The apparatus 10 may also be used as a general purpose gas detector. The apparatus 10 is the only hydrocarbon gas detector that combines a visual and ultraviolet light source in combination with the highly sensitive hydrocarbon gas detector 26. Many flammable hydrocarbons, which include gasoline, kerosene and paint solvents, are often used as accelerants. Investigation of these arson fires can be greatly enhanced if the presence and locations or residual accelerants can be detected at the site as soon as possible. Some other accelerants that can be detected by the apparatus 10 are Acetone, Acrylonitrile, Ammonia, Benzene, Butane, Chloropicrin, Dimethyl Amine, Ethane, Ethanol, Ethylene, Ethylene Oxide, Formaldehyde, Freon 11, Freon 113, Freon 12, Freon 22, Freon 502, Halon 1211, Halon 1301, Hexane, Methane, Methanol, Methyl Acetate, Methyl Chloride, Methyl Ketone, Methyl Mercaptan, Methylene Chloride, Naphtha, Pentane, Propane, Sulfur Dioxide, Trichlorethylene, Trichlorethane, Vinyl Chloride.

The apparatus 10 can be useful in isolating areas of high hydrocarbon concentrations from which "hot" samples that may be collected for further lab analysis. Applications include arson investigation, gas leak detection, locating gasoline spills, detecting HAZMAT cleanup certification, building inspections, detection of bloodstains, semen stains, fugitive gas emissions, and air contaminants.

Figure 12:
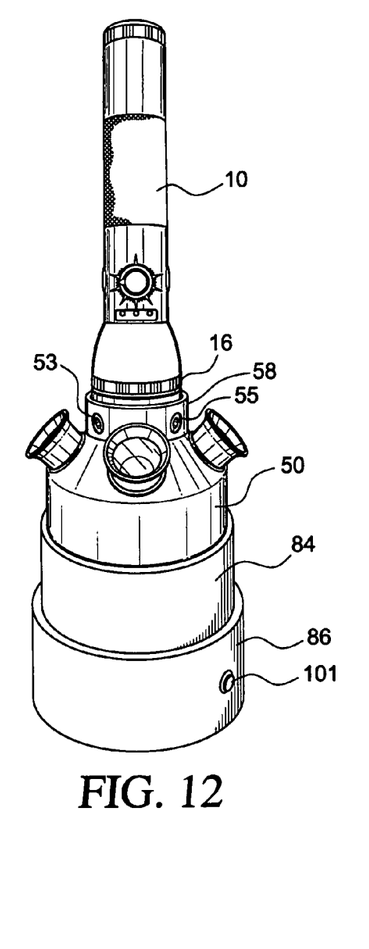
FIG. 12 illustrates a rear perspective view of the arson and forensic scanner and hydrocarbon detector apparatus with the collector cone, the extender sleeve and the collector cone heater chamber all mounted together in accordance with the first embodiment of the present invention.

FIG. 12 illustrates a rear perspective view of the arson and forensic scanner and hydrocarbon detector apparatus 10 in the first embodiment. The collector cone 50 is friction fitted to the apparatus 10 through the front section 16 and the circular top portion 58 with the gripper grommets 53, 55, and 57. The extender sleeve 84 is attached to the collector cone 50 and the collector cone heater chamber 86. At the back of the collector cone heater chamber 86 is a push button activator 101.

Figure 13:
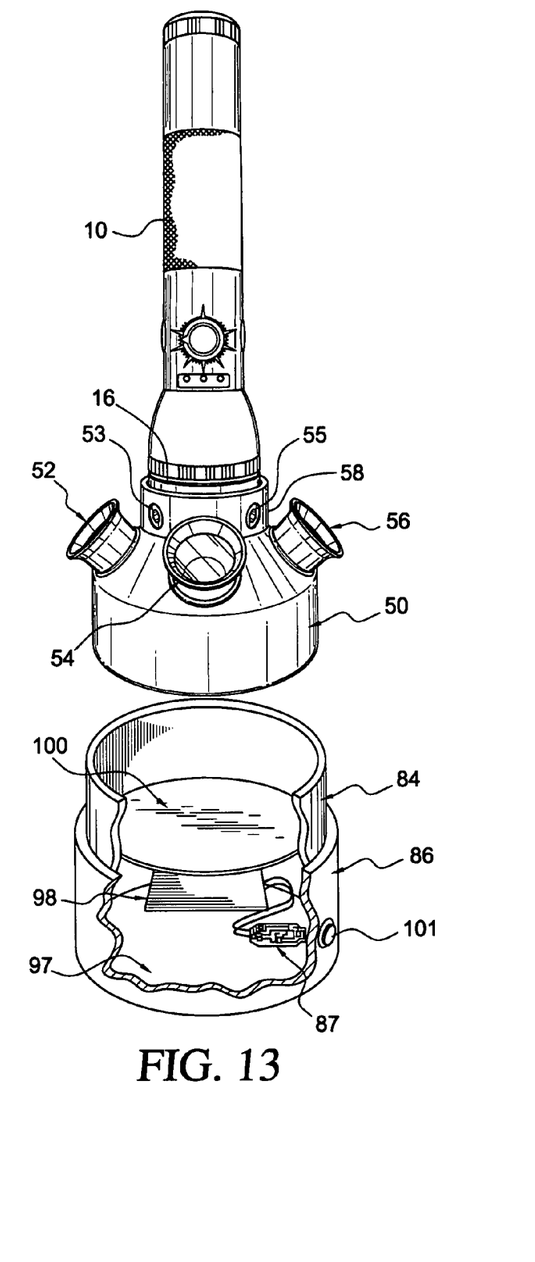
FIG. 13 illustrates a partially exploded rear perspective view of the arson and forensic scanner and hydrocarbon detector apparatus with the collector cone, the extender sleeve and the collector cone heater chamber, and the extender sleeve and the collector cone heater chamber cut away in accordance with the first embodiment of the present invention.

FIG. 13 illustrates a partially exploded rear perspective view of the arson and forensic scanner and hydrocarbon detector apparatus 10 in the first embodiment. The front section 16 of the apparatus 10 is friction fitted into the collector cone 50 by way of the circular top portion 58 and the rubber gripper grommets 53, 55, and 57. The collector cone 50 is then placed inside the extender sleeve 84, which in turn is placed into the collector cone heater chamber 86. Between the chamber 86 and the extender sleeve 84 is the aluminum deck 100 for placing the investigating material. The collector cone heater chamber 86 shown in a cut away includes the battery compartment 97, the timing circuit 87 and the thermo electric heater/cooler 98.

With respect to the second embodiment and when using the collector cone 50 with apparatus 110, arson material can be viewed through the various magnifying lens 52, 54 and 56, the lenses help detect various suspect materials that tend to exhibit different and unique colors under the influence of the various lights provided by the apparatus 110. In the following figure, only one lens 54 is shown. Burnt materials can be viewed by placing the collector cone 50 on the material and turning on the lights of the apparatus 10. The lights from LED arrays 131 and 132 are visible, infrared, ultraviolet or various combinations. Many materials have visual characteristics that are altered when exposed to different temperature and lights. The apparatus 110 is portable and weighs less than one pound. In fact, with the collector cone 50 attached the apparatus 110 the weight approximately one pound and 7.6 ounces. Thus, making the apparatus 110 with the collector cone 50 extremely easy to use and carry in the field during arson or forensic investigations.

Figure 14:
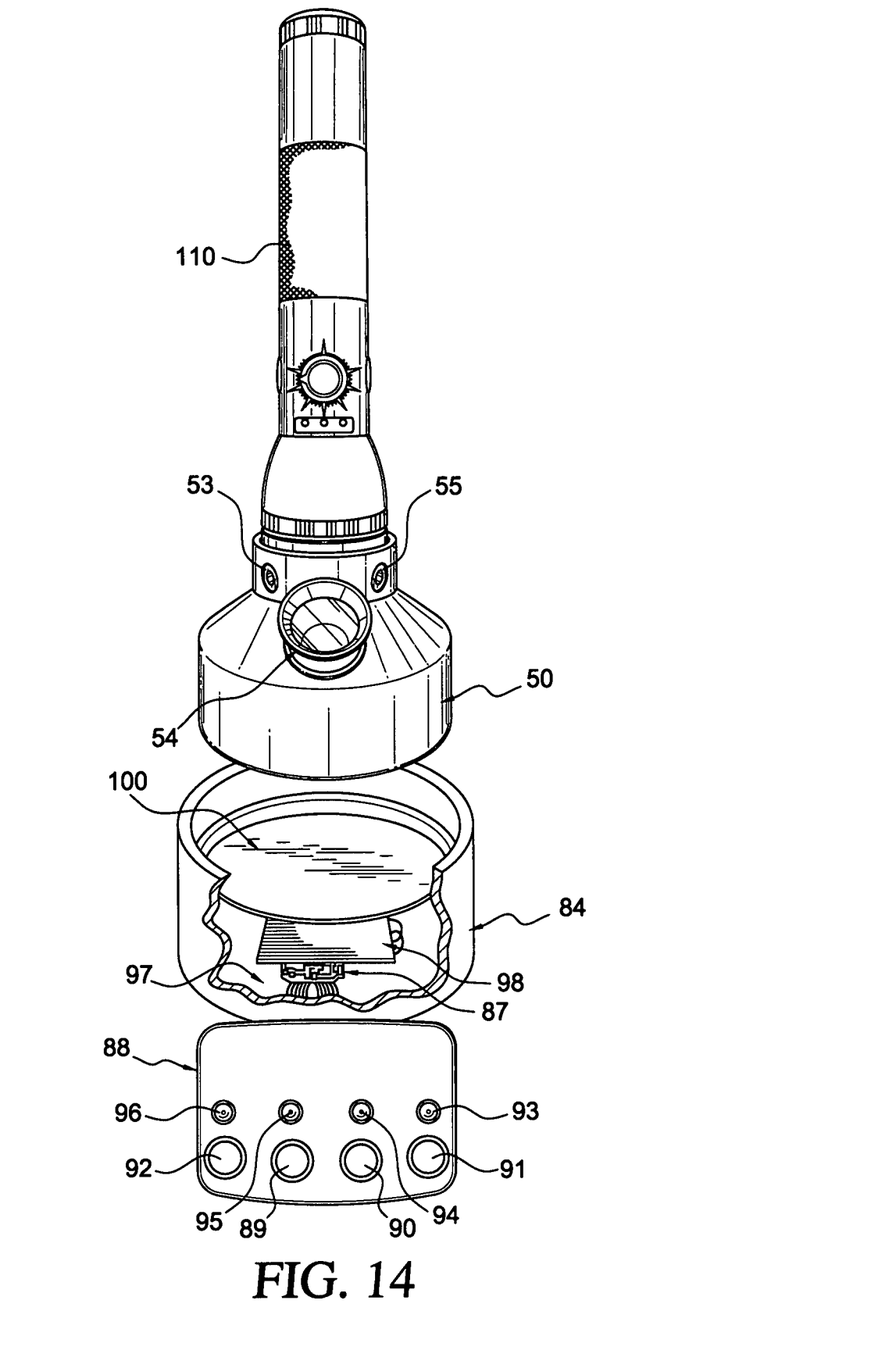
FIG. 14 illustrates a partially exploded perspective view of the arson and forensic scanner and hydrocarbon detector apparatus with the collector cone, the extender sleeve and the collector cone heater chamber and the collector cone heater chamber cut away in accordance with the second embodiment of the present invention.

FIG. 14 illustrates a partially exploded perspective view of the arson and forensic scanner and hydrocarbon detector apparatus 110 with the collector cone 50 and the collector cone heater chamber 86 and the collector cone heater chamber 86 cut away in accordance with the first embodiment of the present invention. The collector cone heat chamber 86 can be used to provide heat or cold to suspect material or a piece of burnt material 76 that may contain entrapped hydrocarbons or other material of interest. When heat is applied to most suspected materials 76, any entrapped hydrocarbons will volatize off, thus enhancing the detection of fugitive hydrocarbons. The collector cone heater chamber 86 includes a timing circuit 87 is equipped with timers that provide five minutes, ten minutes or fifteen minutes of heat or cold. A visible label 88 has a button 89 for the five minute timer, a button 90 for the ten minute timer, and a button 91 for the fifteen minute timer. Each of the buttons 89, 90 and 91 are electrically connected to the timing circuit 87. The label 88 also includes a reset button 92 for resetting the timing circuit 87. There are mode indicator LEDs 93, 94 and 95, above each of the timing buttons 89, 90 and 91 light 93 for visible indicate to the user which of the timers are on. The reset button 92 has its own indicator LED 96 for indicating the reset mode is on to the user. The collector cone heater chamber 84 has a battery compartment 97 to power the timing circuit 87 and a thermo electric heater/cooler module 98. An aluminum deck 100 will heat up or cool down once the thermo electric heater/cooler module 98 is activated. The apparatus 110 is attached to the collector cone 50, which is then attached to the extender sleeve 84. The extender sleeve 84 then fits inside the collector cone heater chamber 84 after the suspect material 86 is placed in the collector cone heater chamber 84. At this point, the investigator 70 can either heat up or cool down the thermo electric heater/cooler module 98 and view the material 76 through one or all of the magnifying lenses 52, 54, 56. In this figure, only one magnifying lens 54 is shown.

Figure 15:
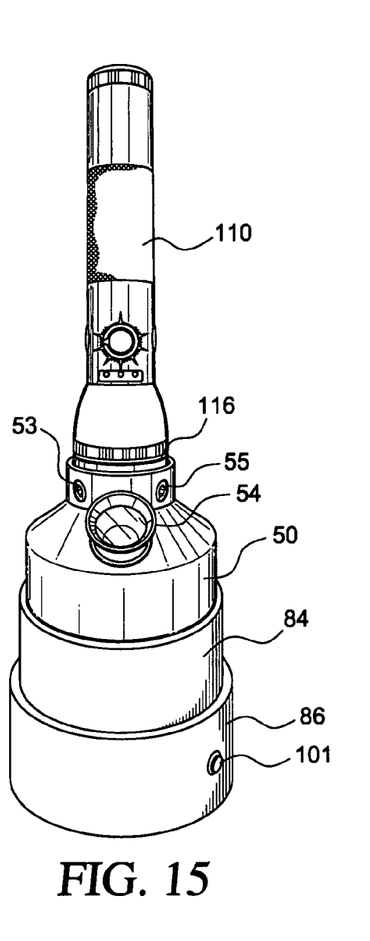
FIG. 15 illustrates a rear perspective view of the arson and forensic scanner and hydrocarbon detector apparatus with the collector cone, the extender sleeve and the collector cone heater chamber all mounted together in accordance with the second embodiment of the present invention.

FIG. 15 illustrates a rear perspective view of the arson and forensic scanner and hydrocarbon detector apparatus 110. The collector cone 50 is friction fitted to the apparatus 110 through the front section 116 and the circular top portion 58 with the gripper grommets 53, 55, and 57. The extender sleeve 84 is attached to the collector cone 50 and the collector cone heater chamber 86. At the back of the collector cone heater chamber 86 is a push button activator 101. In this figure, only one of the magnifier lenses 54 is shown.

Figure 16:
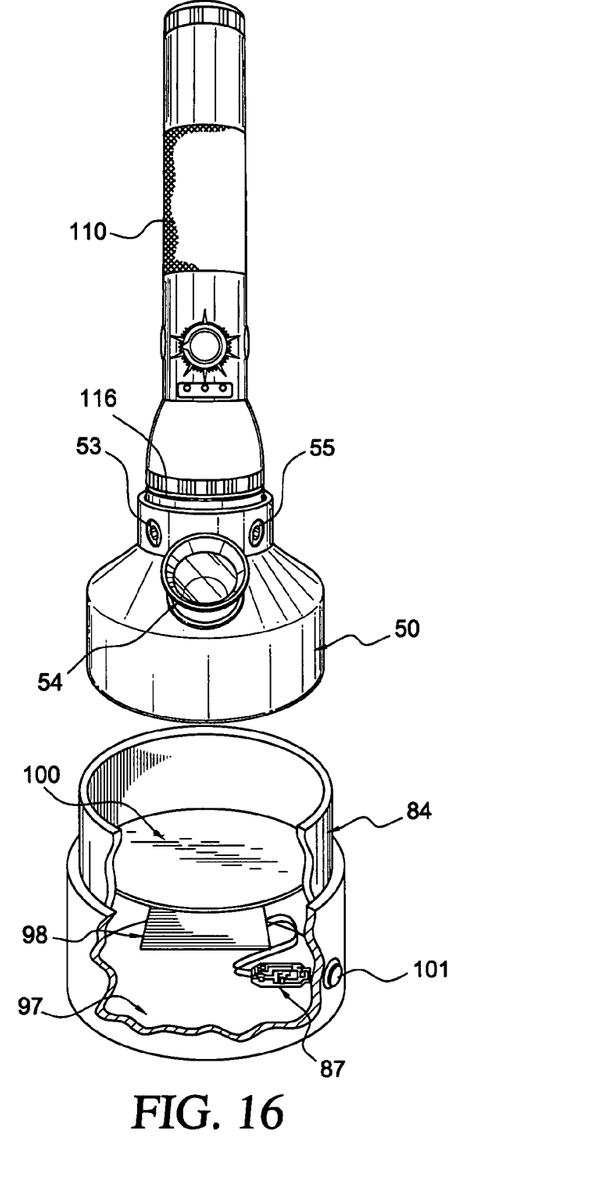
FIG. 16 illustrates a partially exploded rear perspective view of the arson and forensic scanner and hydrocarbon detector apparatus with the collector cone, the extender sleeve and the collector cone heater chamber and the collector cone heater chamber cut away in accordance with the second embodiment of the present invention.

FIG. 16 illustrates a partially exploded rear perspective view of the arson and forensic scanner and hydrocarbon detector apparatus 110 The front section 116 of the apparatus 110 is friction fitted into the collector cone 50 by way of the circular top portion 58 and the rubber gripper grommets 53, 55, and 57. The collector cone 50 is then placed inside the extender sleeve 84, which in turn is placed into the collector cone heater chamber 86. Between the chamber 86 and the extender sleeve 84 is the aluminum deck 100 for placing the investigating material. The collector cone heater chamber 86 shown in a cut away includes the battery compartment 97, the timing circuit 87 and the thermo electric heater/cooler 98.

The collector cone 50 provides a controlled environment for investigating samples. If an accelerant or hydrocarbon is present, the apparatus 110 displays a flashing indicator and audible beep tones. The apparatus 110 is designed so that the more volatile the accelerant then the faster the beep rate. The apparatus 110 has excellent sensitivity and is capable of detecting hydrocarbon concentrations of less than 50 parts per million. The apparatus 10 may also be used as a general purpose gas detector. The apparatus 110 is the only hydrocarbon gas detector that combines a visual and ultra violet (UV) light source in combination with a highly sensitive gas/hydrocarbon detector. Many flammable hydrocarbons, which include gasoline, kerosene and paint solvents, are often used as accelerants. Investigation of these arson fires can be greatly enhanced if the presence and locations or residual accelerants can be detected at the site as soon as possible. Some other accelerants that can be detected by the apparatus 10 are Acetone, Acrylonitrile, Ammonia, Benzene, Butane, Chloropicrin, Dimethyl Amine, Ethane, Ethanol, Ethylene, Ethylene Oxide, Formaldehyde, Freon 11, Freon 113, Freon 12, Freon 22, Freon 502, Halon 1211, Halon 1301, Hexane, Methane, Methanol, Methyl Acetate, Methyl Chloride, Methyl Ketone, Methyl Mercaptan, Methylene Chloride, Naphtha, Pentane, Propane, Sulfur Dioxide, Trichlorethylene, Trichlorethane, Vinyl Chloride.

The apparatus 110 can be useful in isolating areas of high hydrocarbon concentrations from which "hot" samples that may be collected for further lab analysis. Applications include arson investigation, gas leak detection, locating gasoline spills, detecting HAZMAT cleanup certification, building inspections, detection of bloodstains, semen stains, fugitive gas emissions, and air contaminants.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention. For example, although the current description does not provide for LED interchangeability, all LEDs are electronically switched for one array to another and different array colors may be changed depending upon an application of the apparatus 10 or 110. In other words, it may be desirable to have all ultraviolet LEDs or any other type of combination. Also, it may be desirable to simply remove the flashlight head 22 or 122 and interchange them, since the actuation of the LEDs is programmed through the microprocessor.

The invention claimed is:

1. An arson and forensic scanner and hydrocarbon gas detector apparatus, comprising:
    a rear section including a screw off cap for inserting a power supply for supplying power to the apparatus;
    a front section including a flashlight head with a captive hood for capturing gas or volatiles and having a removable circular illumination section including at least thirty-two LEDs for influencing hydrocarbons to fluoresce;
    a hydrocarbon sensor for detecting trace amounts of accelerants and mounted in a center of the circular illumination section;
    a middle section including a hydrocarbon sensitivity control switch, the sensitivity control switch being dial controlled and adjustable over a specific range with viewable graduations, for activating the arson and forensic scanner and hydrocarbon detector, and the hydrocarbon sensitivity switch electrically connected to the hydrocarbon sensor, and a viewable tip bar indicator positioned above the viewable graduations, the viewable tip bar indicator for indicating the thirty-two LEDs are active, the hydrocarbon sensor is ready, and the power supply is low;
    a light button, positioned on one side of the sensitivity control switch, for operating the thirty-two LEDs; and
    an electronic purge button, positioned on the other side of the sensitivity control switch, for purging the hydrocarbon sensor after exposure to hydrocarbon gas.

2. The arson and forensic scanner and hydrocarbon gas detector apparatus of claim 1, further comprising:
    a readily attachable collector cone with a plurality of removable magnifying lenses for viewing the hydrocarbons;
    an extender sleeve for extending the collector cone; and
    a collector cone chamber for receiving the hydrocarbons for viewing through the collector cone.

3. The arson and forensic scanner and hydrocarbon gas detector apparatus of claim 2, wherein the collector cone provides an environmental chamber, which permits easy detection of gaseous vapors and insures a defined environment for hydrocarbon detection; the removable magnifier lens include a power two lens, a power five lens, and a power ten lens, the collector cone includes a circular top portion, which receives the front section of the apparatus forming a secure snug friction fit with rubber gripper grommets.

4. The arson and forensic scanner and hydrocarbon gas detector apparatus of claim 1, wherein the thirty-two LEDs for influencing hydrocarbons to fluoresce including
    a plurality of inter arrays made up of sixteen LEDs spaced around the hydrocarbon sensor, the plurality of inter arrays including blue LEDs, amber LEDs, red LEDs, and green LEDs; and a plurality of outer rings made up of sixteen LEDs spaced around the plurality of inter arrays, the plurality of outer rings including ultraviolet LEDs, and white LEDs.

5. The arson and forensic scanner and hydrocarbon gas detector apparatus of claim 4, the arson and forensic scanner and hydrocarbon gas detector apparatus further comprising:
an electronic circuit positioned in the apparatus, the electronic circuit including a programmable microprocessor for selecting color frequencies for the thirty-two LEDs, the programmable microprocessor being controllable by the light push button for turning "on" and "off" the inter arrays and outer rings of LEDs by mixing different wavelengths of light and colors in combination with the hydrocarbon gas sensor; and
the light button activating the eight white LEDs of the second outer ring with a first push, activating the eight ultraviolet LEDs of the first outer ring with a second push, activating the four blue LEDs of the first inter array with a third push, activating the four red LEDs of the third inter array with a fourth push, activating the four green LEDs of the fourth inter array with a fifth push, activating the four amber LEDs of the second with a sixth push, and controlling power to the apparatus with a seventh push.

6. The arson and forensic scanner and hydrocarbon gas detector apparatus of claim 5, wherein;
said programmable microprocessor also for controlling the thirty-two LEDs by mixing different wavelengths of light and colors emitted; and
said apparatus further comprising
a master power switch for activating a voltage up converter to boost a +3V supply voltage to a +5V supply; and
a multiplexer for activating the hydrocarbon sensor.

7. The arson and forensic scanner and hydrocarbon gas detector apparatus of claim 1, comprising:
a sound port positioned in the circular illumination section amongst the thirty-two LEDs.

8. The arson and forensic scanner and hydrocarbon gas detector apparatus of claim 1, comprising:
a programmable microprocessor for controlling the thirty-two LEDs by mixing different wavelengths of light and colors emitted from the thirty-two LEDs, for receiving code encryption of ultraviolet, infrared, and white light, and for mixing the ultraviolet, the infrared and the visible light;
a master power switch for activating a voltage up converter to boost a +3V supply voltage to a +5V; and
a multiplexer for activating the hydrocarbon sensor.

9. The arson and forensic scanner and hydrocarbon gas detector apparatus of claim 8, wherein the light button controlling the ultraviolet LEDs and the white LEDs with a first push, controlling the infrared LEDs with a second push, and controlling power to the apparatus with a third push.

10. An arson and forensic scanner and hydrocarbon gas detector apparatus, comprising:
a rear section including a screw off cap for inserting a power supply for supplying power to the apparatus;
a front section including a flashlight head with a captive hood for capturing gas or volatiles and having a removable circular illumination section including a hydrocarbon sensor for detecting trace amounts of accelerants, a plurality of inter arrays made up of sixteen LEDs spaced around the hydrocarbon sensor, the plurality of inter arrays including blue LEDs, amber LEDs, red LEDs, and green LEDs, a plurality of outer rings made up of sixteen LEDs spaced around the plurality of inter arrays, the plurality of outer rings including ultraviolet LEDs, and eight LEDs,
a middle section including a hydrocarbon sensitivity control switch, the sensitivity control switch being dial controlled and adjustable over a specific range with viewable graduations, for activating the arson and forensic scanner and hydrocarbon detector, and the hydrocarbon sensitivity switch electrically connected to the hydrocarbon sensor, and a viewable tip bar indicator positioned above the viewable graduations, the viewable tip bar indicator for indicating the plurality of inter arrays and the plurality of outer rings are active, the hydrocarbon sensor is ready, and the power supply is low;
a light button, positioned on one side of the sensitivity control switch, for operating the plurality of inter arrays and the plurality of outer rings; and
an electronic purge button, positioned on the other side of the sensitivity control switch, for purging the hydrocarbon sensor after exposure to hydrocarbon gas.

11. The arson and forensic scanner and hydrocarbon gas detector apparatus of claim 10, further comprising:
a readily attachable collector cone with a plurality of removable magnifying lenses for viewing the hydrocarbons, the plurality of removable magnifier lens include a power two lens, a power five lens, and a power ten lens, and a circular top portion, which receives the front section of the apparatus forming a secure snug friction fit with rubber gripper grommets;
an extender sleeve for extending the collector cone; and
a collector cone chamber for receiving the hydrocarbons for viewing through the collector cone, wherein the collector cone chamber provides an environmental chamber, which permits detection of gaseous vapors and insures a defined environment for hydrocarbon detection.

12. The arson and forensic scanner and hydrocarbon gas detector apparatus of claim 10, comprising:
a sound port positioned in the circular illumination section amongst the plurality of inter arrays and the plurality of outer rings.

13. The arson and forensic scanner and hydrocarbon gas detector apparatus of claim 10, the arson and forensic scanner and hydrocarbon gas detector apparatus further comprising:
an electronic circuit positioned in the apparatus, the electronic circuit including a programmable microprocessor for selecting color frequencies for the plurality of inter arrays and the plurality of outer rings, the programmable microprocessor being controllable by the light push button for turning "on" and "off" the plurality of inter arrays and the plurality of outer rings by mixing different wavelengths of light and colors in combination with the hydrocarbon gas sensor; and
the light button activating the eight white LEDs with a first push, activating the eight ultraviolet LEDs with a second push, activating the four blue LEDs with a third push, activating the four red LEDs with a fourth push, activating the four green LEDs with a fifth push, activating the four amber LEDs with a sixth push, and controlling power to the apparatus with a seventh push.

14. The arson and forensic scanner and hydrocarbon gas detector apparatus of claim 10, further comprising;
a pre-programmable microprocessor for controlling the thirty-two LEDs by mixing different wavelengths of light and colors emitted;

a master power switch for activating a voltage up converter to boost a +3V supply voltage to a +5V supply; and a multiplexer for activating the hydrocarbon sensor.

15. An arson and forensic scanner and hydrocarbon gas detector apparatus, comprising:

a rear section including a screw off cap for inserting a power supply for supplying power to the apparatus;

a front section including a flashlight head with a captive hood for capturing gas or volatiles and having a removable circular illumination section including at least thirty-two LEDs of ultraviolet, white and infrared LED arrays for influencing hydrocarbons to fluoresce;

a hydrocarbon sensor for detecting trace amounts of accelerants and mounted in a center of the circular illumination section;

a middle section including a hydrocarbon sensitivity control switch, the sensitivity control switch being dial controlled and adjustable over a specific range with viewable graduations, for activating the arson and forensic scanner and hydrocarbon detector, and the hydrocarbon sensitivity switch electrically connected to the hydrocarbon sensor, and a viewable tip bar indicator positioned above the viewable graduations, the viewable tip bar indicator for indicating the thirty-two LEDs are active, the hydrocarbon sensor is ready, and if the power supply is low;

a light button, positioned on one side of the sensitivity control switch, for operating the thirty-two LEDs; and an electronic purge button, positioned on the other side of the sensitivity control switch, for purging the hydrocarbon sensor after exposure to hydrocarbon gas.

16. The arson and forensic scanner and hydrocarbon gas detector apparatus of claim 15, further comprising: a readily attachable collector cone with a plurality of removable magnifying lenses for viewing the hydrocarbons; an extender sleeve for extending the collector cone; and a collector cone chamber for receiving the hydrocarbons for viewing by the collector cone, wherein the collector cone provides an environmental chamber, which permits easy detection of gaseous vapors and insures a defined environment for hydrocarbon detection; the readily removable magnifier lens include a power two lens, a power five lens, and a power ten lens, the collector cone includes a circular top portion, which receives the front section of the apparatus forming a secure snug friction fit with rubber gripper grommets.

17. The arson and forensic scanner and hydrocarbon gas detector apparatus of claim 15, comprising:

a sound port positioned in the circular illumination section amongst the thirty-two LEDs.

18. The arson and forensic scanner and hydrocarbon gas detector apparatus of claim 15, wherein the light button controlling the ultraviolet LEDs and the white LEDs with a first push, controlling the infrared LEDs with a second push, and controlling power to the apparatus with a third push.

* * * * *